US010822609B2

(12) United States Patent
Grossi de Sá et al.

(10) Patent No.: US 10,822,609 B2
(45) Date of Patent: Nov. 3, 2020

(54) GENETIC CONTROL METHOD AND COMPOSITIONS AGAINST INSECT PESTS IN COTTON PLANTS BY THE SILENCING OF GENES OF THE LACCASE FAMILY

(71) Applicants: EMPRESA BRASILEIRA DE PESQUISA AGROPECUÁRIA—EMBRAPA, Brasilia-DF (BR); Universidade Federal do Rio Grande do Sul, Porto Alegre, RS (BR)

(72) Inventors: Maria Fátima Grossi de Sá, Brasilia-DF (BR); Alexandre Augusto Pereira Firmino, Brasilia-DF (BR); Maria Cristina Mattar da Silva, Brasilia-DF (BR); Diogo Martins de Sá, Brasilia-DF (BR); Roberta Ramos Coelho, Brasilia-DF (BR); Leonardo Lima Pepino de Macedo, Brasilia-DF (BR); Isabela Tristan Lourenco, Brasilia-DF (BR)

(73) Assignees: EMPRESA BRASILEIRA DE PESQUISA AGROPECUÁRIA—EMBRAPA, Brasília (BR); Universidade Federal do Rio Grande do Sul, Porto Alegre, RS (BR)

( * ) Notice: Subject to any disclaimer, the term of this patent is extended or adjusted under 35 U.S.C. 154(b) by 102 days.

(21) Appl. No.: 14/655,097

(22) PCT Filed: Dec. 27, 2013

(86) PCT No.: PCT/BR2013/000607
§ 371 (c)(1),
(2) Date: Aug. 19, 2015

(87) PCT Pub. No.: WO2014/100878
PCT Pub. Date: Jul. 3, 2014

(65) Prior Publication Data
US 2015/0368649 A1 Dec. 24, 2015

(30) Foreign Application Priority Data
Dec. 28, 2012 (BR) ............... 102012033506

(51) Int. Cl.
*C12N 15/82* (2006.01)
*C12N 15/113* (2010.01)
*A01N 43/54* (2006.01)

(52) U.S. Cl.
CPC .......... *C12N 15/1137* (2013.01); *A01N 43/54* (2013.01); *C12N 15/113* (2013.01); *C12N 15/8218* (2013.01); *C12N 15/8286* (2013.01); *A23V 2002/00* (2013.01); *C12N 2310/14* (2013.01); *C12N 2310/141* (2013.01); *Y02A 40/162* (2018.01)

(58) Field of Classification Search
CPC .................................................. C12N 15/1137
USPC ....................................................... 800/279
See application file for complete search history.

(56) References Cited

U.S. PATENT DOCUMENTS

2007/0271630 A1 11/2007 Boukharov et al.
2012/0240288 A1* 9/2012 Ye ...................... C12N 15/8218
800/279

OTHER PUBLICATIONS

GenBank Accession AY884062, 2008.*
Smith et al. 2000, Nature, 407:319-320.*
Fourgoux-Nicol et al 1999, Plant Molecular Biology 40 :857-872.*
Thomas et al. 2001, The Plant Journal 25(4):419-425.*
Colliver et al. Plant Molecular Biology 35:509-522.*
Yibrah et al. 1993 Hereditas 118:273-280.*
Arakane et al Proc. Natl. Acad. Sci. U.S.A. 102 (32), 11337-11342 (2005).*
"GenBank Accession DQ062153.1", Basic Local Alignment Search Tool, Jun. 27, 2008, 4 pages.
James A. Baum, et al., "Control of coleopteran insect pests through RNA interference", Nature Biotechnology, Nov. 2007, pp. 1322-1326, vol. 25, No. 11.
Hanneke Huvenhe, et al., "Mechanisms of dsRNA uptake in insects and potential of RNAi for pest control: A review", Journal of Insect Physiology, 2010, pp. 227-235, vol. 56.
International Search Report for PCT/BR2013/000607 dated Aug. 26, 2014 [PCT/ISA/210].
Written Opinion for PCT/BR2013/000607 dated Aug. 26, 2014 [PCT/ISA/237].

* cited by examiner

*Primary Examiner* — Li Zheng
(74) *Attorney, Agent, or Firm* — Sughrue Mion, PLLC (57) ABSTRACT

The present invention relates to the control of infestation of pests by inhibiting or reducing the expression of genes of the family of chitin synthase. The invention further provides methods and compositions for controlling pests by feeding them with one or more double-strand RNA molecules provides by the present invention. The invention further describes a method of obtaining transgenic plants that express double-strand RNA molecules. The present invention is preferably used for cotton-plants.

35 Claims, 4 Drawing Sheets
Specification includes a Sequence Listing.

SEQUENCE LISTING

<160> NUMBER OF SEQ ID NOS: 4

<210> SEQ ID NO 1
<211> LENGTH: 1817
<212> TYPE: DNA
<213> ORGANISM: Anthonomus grandis

<400> SEQUENCE: 1

```
atattttgag atactacaag ggaccatata ctccattcac ccaagcacct acttatgact      60
tcggtattcc acagggagtg gwacttaatc ctttggacgc aatttgtaat gaaaccagag     120
cagatgccgt ttgtatcagt caattgaaaa atgccagaga agtggacagg gcgctgctga     180
ttgaaaaacc aaatgtgaag atattttgc cattcagatt ccacgtttat acaccggagg     240 atcttttaa tcctaacagt tacaacagac atttagttgc gccaaacgga gaccacgtaa     300
tcagtttaat cgacgaaatc tcgtacatgg ctgcgccagc tccgcttcta tctcagtacg     360
atgaaattga ccccgagcaa ttctgtaatg gagataacag accacccaat tgtggaccta     420
actgcatgtg tacccacaaa attgatattc cattaaatgc gattgtcgaa gttgttctgg     480
ttgatgaagt tcaacaaccg aacttatccc atccgttcca tttgcacggt tatgcttta      540
```

```
atgtggtcgg tattggtcgc tcacctgaca caagtgtcaa gaaaattaac ttaaaacacg      600
ctttggatct ggatcggaga ggtctgttgc ataggcactt tgatctgcca cccggtaaag      660
acaccattgc tgtaccaaac aatggatacg taatcttcag attccgagca gacaatcctg      720
gtttctggct tttccactgt cacttcttgt tccacatagt tataggaatg aatttggtcc      780
tgcaagtggg tacacatgca gacataccac cagtgccacc gaatttccct acttgcggcg      840
atcacacgcc acgaatcaat ttagatccaa cgaaaatatg aagacttaat acctagtatt      900
ttttttaaga ttaagggtcc ttttttagtat aggttggtgt aaataagagt caagtcaaag     960
gtttggtaag tattacgagt taatatattt tgtgaaaaaa tgtacagggt tatgctactc     1020
atgtatatta tttcaggtag gtataataac gcaatgtata taatttttta ctagcacaat     1080
attgtaaata taacatattt acacgatctt atttgtcacc aactgctagt atattgtaga     1140
gttaccaaat taatattctg aatatttgga ttaagtcttg ccatccaaaa atgtcgaaaa     1200
atcagtattc taaattgagt gttttcctat attatgtatt ttatttatct gatatttatc     1260
tgtactgtac caaatggtct ttatcgccat attattatat ataattttag atattctacc     1320
tctttctatg tgttttwtttt ttgttttttt taactatcac tattggtgct ttctaaaact     1380
tataaatcaa ttatttgagt taaaatcttt aaatattttt tgatactttt cataataaga     1440
aaaatgtttt ggttaatatt tttaatatgg gaaatattta aagatttaaa ggtatgaacc     1500
ctttcgtaaa taaattattt cttccaggaa gtaagctaag gtctttaatg taaaaattct     1560
tatagttata gtagaaattt tatgattatg tcattggaaa tgttaccaac ataacgaagt     1620
aaataaatat gaattttatc acatctatac cacaaaaata ggcacttcat agtacatttt     1680
ttggtaaaag aaccacctag tctattacaa aaccaagacg aatatgaaaa taagtcatcg     1740
ttgtagattt gtatataaaa taatagtgta aagtaccaat gtatttaaag taataaaatt     1800
tgtgactata tttatgt                                                   1817

<210> SEQ ID NO 2
<211> LENGTH: 332
<212> TYPE: DNA
<213> ORGANISM: Anthonomus grandis

<400> SEQUENCE: 2
gctccgcttc tatctcagta cgatgaaatt gaccccgagc aattctgtaa tggagataac       60
agaccaccca attgtggacc taactgcatg tgtacccaca aaattgatat tccattaaat      120
gcgattgtcg aagttgttct ggttgatgaa gttcaacaac cgaacttatc ccatccgttc      180
catttgcacg gttatgcttt taatgtggtc ggtattggtc gctcacctga cacaagtgtc      240
aagaaaatta acttaaaaca cgctttggat ctggatcgga gaggtctgtt gcataggcac      300
tttgatctgc cacccggtaa agacaccatt gc                                    332

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3 gctccgcttctatctcagt                                                     19

<210> SEQ ID NO 4
```

```
<211> LENGTH: 18
<212> TYPE: DNA
<213> ORGANISM: Artificial Sequence
<220> FEATURE:
<223> OTHER INFORMATION: Primer

<400> SEQUENCE: 4 gcaatggtgtctttaccg                                                  18
```

GENETIC CONTROL METHOD AND COMPOSITIONS AGAINST INSECT PESTS IN COTTON PLANTS BY THE SILENCING OF GENES OF THE LACCASE FAMILY

FIELD OF THE INVENTION

The present invention relates to the field of control of insect pests that attack crops, especially cotton plants, by silencing genes of the family of laccase, through mediation of double-strand RNA (dsRNA) expressed in cotton plants.

BACKGROUND OF THE INVENTION

The world agricultural production has received special attention in the early twenty-first century. The growing demand for food and agricultural products and the projections of world population growth in the coming decades requires the development of methodologies and sustainable processes that will help meet this demand by increasing agricultural production, particularly in developing countries in Africa, Asia and Latin America. In Brazil, agribusiness is the most important sector of the national economy, accounting for over one third of GDP (Gross Domestic Product), 37% of jobs created in the country and 41% of our exports in 2012 according to the Ministry of Agriculture.

Despite the application of more than 2.5 million tons of pesticides in the world, it is estimated that over 25% of the entire production potential is still lost due to pest attack, including insects, weeds, herbs and plant pathogens before harvest. For some commodity such as rice, potatoes and maize, this loss varies between 30 and 40%. In addition to the losses, the use of pesticides represents a cost of more than 10 billion dollars a year. Pest control with chemicals greatly diminished the damage caused by insects and pathogens in the last five decades. However, the widespread, extensive and continuous use of chemical pesticides can result in environmental degradation, harmful effects on human health and other organisms, and harm nontarget organisms, leading to selection for populations of resistant pests. In this context, biotechnology is an area that has excelled in the promising task of providing new products, processes and methodologies to increase agricultural production, not only with the development of inputs, but also varieties resistant to abiotic stresses such as temperature, drought, salinity and biotic stresses such as pest attack and diseases. Genetic engineering tools gave humans an unprecedented power to manipulate and develop new plant genotypes, in addition to providing a promising avenue for a more secure and sustainable agriculture. Genes from plants and other organisms involved in regulating signaling pathways of important physiological processes have been cloned and transferred to plants of agronomic interest, conferring new economically important traits for increasing production.

In this sense, the use of genetically modified (GM) plants for insect control has been one of the most effective methods in recent years. Since the early adoption of this technology in 1996, there was an increase of 1,7 million to 160 million in 2011, making it the fastest adopted technology in the history of modern agriculture (JAMES C. Global Status of Commercialized Biotech/GM Crops: 2011 ISAAA Brief No. 43 ISAAA: Ithaca, N.Y., v 43, 2011.ISSN 978-1-892456-52-4). According to the Center for Environmental Risk Assessment (CERA-Washington, D.C.) that monitors the global release of GM varieties, 59 varieties—corn, soybeans, cotton, tomato and potato—developed for insect resistance are currently planted in various countries (CERA, C.F.E.R.A. GM Crop Database. Washington, D.C. USA, Jun. 2012 2012. Available at: cera-gmc.org/, Access: 10-07-2012). Cotton cultivars resistant to lepidopteran larvae and corn cultivars resistant to Lepidoptera and Coleoptera have been used in the world agriculture, reducing the use of pesticides and decreasing production costs (James, C. Commercialized Global status of biotech/GM Crops: 2011 ISAAA Brief No. 43 ISAAA: Ithaca, N.Y., v 43, 201 1. ISSN 978-1-892456-52-4). The use of genetic engineering brought advantages in relation to classical genetic methods. Besides increasing the search for potential genes involved in characteristics of interest provides for introduction of a number of different genes in the same plant, reducing the time characteristics of introgression in a desired genetic elite event.

Thus, the introduction of genes involved in the response of other plants to the insect, or genes encoding insecticidal proteins, or whose product interferes with the development of insect pests may be a fast and efficient way to improve commercial varieties.

Cotton crop is the most important of textile fiber crops, cotton being one of the most cultivated plant species in the world. In addition to the primary cotton products (feather, stone and fibril), the production chain produces cotton-based lint, yarn, fabric, knitwear, pie, meal, crude oil and biodiesel and has a turnover of billion dollars in world trade (NEVES, M. F.; PINTO, M. J. A. A CADEIA DO ALGODÃO BRASILEIRO: DESAFIOS E ESTRATÉGIAS [BRAZILIAN COTTON CHAIN: CHALLENGES AND STRATEGIES] Brasília—DF: Markestrat, 2012). In Brazil, cotton crop is ranked among the top ten agricultural crops. In the world scenario, the country stands out: it is the fourth largest producer in the world. Despite the subtle decrease in production due to weather problems, cotton production in Brazil is quite affected by the action of pests and diseases that impair the quality of agricultural products derived from cotton production, affecting not only the primary sector (production) but also the secondary (manufacturing, marketing and export) and tertiary (services). Pests, diseases and weeds are difficult to control and cause damage to the cotton plants, increasing the cost of production due to the large use of agricultural pesticides. The reduction in costs with agricultural pesticides depends on development, transfer and use of more efficient technologies to combat pests, diseases and weeds.

In Brazil, there are 20 pests of economic importance to the cotton farmer and 5 occasional pests, in addition to 15 diseases caused by fungi, bacteria, viruses and nematodes (FREIRE, E. C. Algodão no Cerrado. 2nd Edition Revised. Brasília—DF:ABRAPA—Brazilian Association of Cotton producers, 2011). The main insect pests that infest cotton crops are the tobacco budworm—*Heliothis virescens* Fabr., 1781 (Lepidoptera: Noctuidae), the Pink bollworm—*Pectinophora gossypiella* Saund, 1844 (Lepidoptera—Gelechiidae), the Leafworm—*Alabama argillacea* Hubner., 1818 (Lepidoptera: Noctuidae), the Boll weevil—*Anthonomus grandis* Boh., 1843 (Coleoptera: Curculionidae) and the Fall armyworm—*Spodoptera frugiperda* J E Smith, 1797 (Lepidoptera: Noctuidae). In order to combat them, producers may perform up to 30 pesticide applications, mostly to combat aphids, caterpillars and the boll weevil, the latter being largely responsible for the decrease in the production between the 1980s and 1990s when it destroyed whole crops in regions of the northeast, southeast and south of Brazil. The boll weevil (*Anthonomus grandis* Boheman, 1843) is one of the most important insect pests of cotton crops, being responsible for considerable damage to crops in several countries of the Americas. It is an insect of the order Coleoptera, of the Curculionidae family, which is usually four to nine millimeters long, the young adult has a brown rust color and it becomes gray when it gets older. A remarkable feature, responsible for the name by which the insect is known, is its elongated, forward-projecting head, which extends in a rostrum which is half of its slim, curved length. The size variation of boll weevil is influenced by a number of factors such as temperature, humidity and amount of food in the larval stage. Some features of boll weevil's life cycle make it difficult to control their population. The adult boll weevil may hibernate during winter (diapause) in crop residues, organic waste from farms and barns. This diapause may last for months, for periods varying from 150-180 days until a new crop cycle. It is estimated that, of each 50 boll weevils in diapause, a population of 500,000 adults will arise at the end of next harvest. In addition, the insect has high mobility, being capable of flying several kilometers, and high tolerance to their natural enemies. Boll weevil's preferred feed is plants of the *Gossypium* genus. However, 104 species of the Maivaceae family are attacked by boll weevil. Species such as *Hibiscus* sp. are considered important to maintain boll weevil population in the cotton off-season.

Currently, studies have been conducted with the aim of generating economic and ecologically viable technologies for the control of this pest. These include: (i) classical breeding in order to develop cultivars with short cycle and fast-maturing, (ii) pheromone traps, and (iii) biological alternatives include the use of biological agents as bacteria, fungi and viruses which may be used by direct spraying or for manipulation and transformation of cotton plants. Plant breeding programs through genetic modification consist of an alternative route to conventional methods for insect-pest control. More than 10 insect-resistant GM cotton plant cultivars are commercialized worldwide. However, none of them is resistant to boll weevil; therefore, they do not control the main pest of cotton crops in Brazil.

The main GM varieties with well-established entomotoxic effects express toxins from *Bacillus thuringiensis*. Currently particular focus has been given to the use of RNA interference (RNAi) for the control of pests (PRICE, D. R.; GATEHOUSE, J. A. RNAi-mediated crop protection against insects Trends in Biotechnology, vol 26, No 7, p. 393-400, 2008). This process, first described in plants, has been referred to as Post-Trancriptional Gene Silencing or PTGS (JORGENSEN et al., 1996). Shortly after, researchers Andy Fire and Craig Mello (FIRE et al., 1998) assigned the term RNA mediated interference, or simply RNA interference (RNAi), to the silencing of a specific gene of *C. elegans* for a particular nucleotide sequence caused by the application of exogenous double-stranded RNA (dsRNA). Just over a decade after RNAi was discovered, small RNAs involved in mechanism of RNAi-induced silencing are defined not only by their sizes (~20-30 nucleotides) but also by their association with proteins of the Argonaute family (GHILDIYAL; ZAMORE, 2009; KETTING, 2011). The Argonaute family is characterized by proteins characterized by proteins that possess the conserved domains PAZ and PIWI. The domain PAZ is the specific binding region to double-stranded RNAs and the domain PIWI has a similar structure to the cleavage domain RNase H. Several studies using RNA interference for functional assessment of a given gene have been conducted in various organisms. These studies vary in dsRNA administration methods and evaluation of the silencing effect. Many studies on insects aim to study the function of a given gene for a better understanding of a physiological process, in most cases, aiming at a biotechnological application. The use of RNAi has been working in various insect cell lines, eggs, larvae and adults with the use of plasmid vectors to express and synthesize dsRNAs which can be administered by feed injection and even electroporation thereby causing target gene silencing and phenotype changes. While many of these studies analyze gene function to understand the biology of insects, most studies, especially of Lepidoptera, Coleoptera and Diptera search genes of biotechnological interest. Widely used for analysis of gene expression, RNA interference is a promising tool in helping to control pests. Its mechanism of action is mainly based on the introduction of a double-stranded RNA in a target organism, by microinjection or ingestion (FIRE et al., 1998). This double stranded RNA initiates a process of post-transcriptional gene silencing by degrading mRNA homologous, causing a decrease in the synthesis of the corresponding protein (MEISTER; TUSCHL, 2004), hindering the survival or even leading to insect death.

Laccase (p-diphenol: dioxygen oxidoreductase, EC 1.10.3.2) are enzymes of the family of multi-copper oxidases, which also includes ascorbate oxidase, L-(dioxygen ascorbate oxidoreductases, EC1.10.3.3) and ferroxidases (Fe(II): dioxygen oxidoreductase, EC1.16.3.1) (DITTMER, N T; KANOST, M R Insect multicopper oxidases: diversity, properties, and physiological roles Insect Biochemistry and Molecular Biology, vol. 40, No. 3, p. 179-88, 2010). They are proteins that contain copper atoms (Cu) which reduce molecular oxygen to form water and simultaneously to oxidize the transfer of a elétron various substrates such as diphenols, methoxy-substituted monophenols and aliphatic and aromatic amines. The main role of laccases described in insects is in sclerotization cuticle, although laccase activities and sclerotization processes can occur in cocoons and eggs. Their presence in the cuticle and the activity related to sclerotization was first described in 1969 (YAMAZAKI, 1969) and their role in the process has been studied in insects since then (DITTMER, N T; KANOST, M R Insect multi-copper oxidases: diversity, properties, and physiological roles. Insect Biochemistry and Molecular Biology, vol. 40, No. 3, p. 179-88, 2010). However, few studies have been published related mechanisms of action and gene and protein characterization of these enzymes. One of the challenges for the study of this class of enzymes in insects is its isolation and purification, especially its solubility. Proteolytic methods have been used to attempt to solubilize the enzyme, but the degree of structural change in the kinetic and physicochemical properties is not unknown relative to the native protein in its medium of action. The importance of laccase during the development makes this enzyme a potential target for biotechnological use in insect control.

SUMMARY OF THE INVENTION

The present invention relates to a method for reducing or inhibiting the expression of a laccase gene in eukaryotic cells, particularly insect cells, resulting in the death, inhibition, atrophy or feed interruption of a target pest. In one embodiment the invention describes nucleic acid molecules substantially similar to sequences selected from SEQ ID NO: 1 and SEQ ID NO: 2, or fragments or complements thereof. The invention describes dsRNA molecules, sequences selected from among SEQ ID NO: 1 and SEQ ID NO: 2, or fragments or complements thereof or fragment or complement thereof stabilized or expression of one or more microRNAs (miRNA) or siRNAs for inhibiting expression of a target gene in coleopteran pest expressed from these sequences and fragments thereof. The invention further discloses compositions containing nucleic acid molecules substantially similar to sequences selected from SEQ ID NO: 1 and SEQ ID NO: 2, or fragments or complements thereof, for the control of insect pests, particularly boll weevil (*Anthonomus grandis*).

The invention also provides a method for suppressing gene expression in a coleopteran pest such as boll weevil or related species, which comprises the step of providing in the diet of the pest a gene suppressive amount, with at least one dsRNA molecule transcribed from a nucleotide sequence substantially similar to sequences selected from SEQ ID NO: 1 and SEQ ID NO: 2, or fragments or complements thereof, that has at least one additional fragment of a sequence of mRNA inside cells of the pest. Further aspects of the invention are chimeric genes, gene constructs containing the nucleic acid molecules of the present invention, transformation and expression vectors, transgenic cells and organisms, methods for expression of the molecule of the invention in transgenic organisms, as well as the use of same in pest control. The invention further comprises a method for obtaining a transgenic plant using the gene constructs of the present invention and a food or feed production method comprising obtaining a plant transformed with polynucleotides having a nucleotide sequence substantially similar to the selected sequences of SEQ ID NO: 1 and SEQ ID NO: 2, or fragments or complements thereof, and preparing food or feed from said plant or part thereof.

DETAILED DESCRIPTION OF THE INVENTION

The present invention describes methods and compositions for the control of pests, especially pests of cotton. For example, the present invention provides recombinant DNA technologies to suppress or inhibit post-transcriptionally the expression of a target sequence in the cell of a pest. This effect is obtained by feeding to one or more pests, double stranded RNA or RNA fragments (miRNA or sRNA) transcripts from all or part of a target coding sequence, thereby controlling the infestation. Therefore, the present invention relates to sequence-specific inhibition of expression of coding sequences using double stranded RNA (dsRNA), including small interfering RNA (siRNA), to achieve the intended levels of pest control.

The present invention provides a method of inhibiting expression of a target gene Coleoptera. In certain embodiments, the method comprises modulating or inhibiting expression of one or more genes-target coleopteran occurs that causes growth inhibition, reproduction and/or infectivity and eventually result in the death of the insect. More specifically, the present invention relates to the inhibition of the laccase gene in beetles, resulting in stopping the growth and malformation of larvae and adults and can result in death of the insect. The method comprises introducing double stranded RNA (dsRNA) partially stabilized, including its modified forms such as small interfering RNA sequences (siRNA) within cells or extracellular medium, such as the midgut or cuticle within coleopteran wherein the body dsRNA enters the cells and inhibits expression of at least one or more target genes and wherein the inhibition exerts a deleterious effect on the pest. The methods and associated compositions may be used to limit or eliminate the infestation of coleopteran or on any pest host, pest symbiont, or environment in which the pest is present by one or more compositions comprising the dsRNA molecule described herein in the diet of the pest.

The present invention further provides examples of nucleic acid compositions that are homologous to at least a portion of sequences selected from SEQ ID NO: 1 and SEQ ID NO: 2, or fragments or complements thereof. A specific example of such nucleic acids In yet another aspect, the invention provides a method for suppression of gene expression in a coleopteran pest, such as boll weevil or related species, comprising the step of providing in the diet of the pest an amount of suppressive gene of at least one dsRNA molecule transcribed from a nucleotide sequence as described herein, at least one segment which is complementary to a miRNA sequence within the cells of the pest. The method may further comprise the death, stunting, or cessation of feeding of the pest. A dsRNA molecule, including its modified form such as an siRNA molecule, fed to a pest in accordance with the invention can be at least about 80, 81, 82, 83, 84, 85, 86, 87, 88 89, 90, 91, 92, 93, 94, 95, 96, 97, 98, 99, or about 100% identity to a RNA molecule transcribed from the sequences selected from SEQ ID No. 1 and SEQ ID No. 2, or fragments or complements thereof.

The present invention further provides a stabilized dsRNA molecule or the expression of one or more miRNAs for inhibition of expression of a target gene in a coleopteran pest expressed from this sequence and fragments thereof. A stabilized dsRNA, including a miRNA or sRNA molecule or the expression of one or more siRNAs may comprise at least two coding sequences that are arranged in a sense and an antisense orientation relative to at least a promoter, wherein the nucleotide sequence comprising a chain sense and antisense strand are linked or connected by a spacing sequence of at least from about five to about one thousand nucleotides, wherein the sense strand and the antisense strand lengths can be formed different, and each of the two parts sequences encoding at least 80% sequence identity, at least 90%, at least 95%, at least 98%, or 100% sequence identity to any sequence of one or more nucleotide (s) according to the sequences selected from SEQ ID No. 1 and SEQ ID No. 2, or fragments or complements thereof.

Moreover, the invention further provides a fragment or concatemer of a nucleic acid sequence selected from the sequences SEQ ID No. 1 and SEQ ID No. 2, or fragments or complements thereof. The fragment may be defined as causing death or impairing the development of a pest when expressed as a dsRNA and provided to the pest. The fragment may, for example, comprise at least about 19, 21, 23, 25, 40, 60, 80, 100, 125, 150, 175, 200, 225, 250, 275, 300, 325 or more contiguous nucleotides of sequences selected from SEQ ID No. 1 and SEQ ID No. 2, or fragments or complements thereof, or a complement thereof. An RNA segment beneficial for use in the present invention is at least about 19 to about 30, or about 23 to about 100 nucleotides to about 2000 nucleotides in length, or more. Particularly useful for the present invention are RNA sequences, including about 19 to about 600 nucleotides homologous to a pest target sequence. The invention also provides a ribonucleic acid expressed from any of such sequences including a dsRNA. The sequence selected for use in the expression of a gene suppression agent can be constructed from a single sequence derived from one or more target pests and intended for use in expression of an RNA that functions in the suppression of a single gene or family gene in one or more target pests, or the DNA sequence can be constructed as a chimera from a plurality of DNA sequences. Specifically for the present invention, this gene family is related to the family of the laccase gene.

In yet another aspect, the invention provides recombinant DNA constructs comprising a nucleic acid molecule encoding a dsRNA molecule described herein. The dsRNA may be formed by a tape transcription of the molecule of a nucleotide sequence that is at least about 80% to about 100% identical to the sequences selected from SEQ ID No. 1 and SEQ ID No. 2, or fragments or complements thereof. Such recombinant DNA constructs may be defined as producing dsRNA molecules capable of inhibiting or reducing the expression of endogenous target gene (s) in a pest cell upon ingestion. The construction can include a nucleotide sequence of the invention operably linked to a promoter sequence that functions in the host cell. The present invention can be used tissue-specific or constitutive promoters. Preferably for the present invention, the tissue-specific promoters may be, but are not limited to, promoters specific for flower buds of cotton plants.

Nucleic acid constructs according to the invention may comprise at least one nucleotide sequence that does not occur naturally and can be transcribed into a single stranded RNA capable of forming a dsRNA molecule in vivo through hybridization. Such dsRNA sequences may be provided in the diet of a coleopteran pest to achieve the desired inhibition. Preferably for the present invention, the dsRNA molecule is formed by nucleotide sequences substantially similar to sequences selected from SEQ ID No. 1 and SEQ ID No. 2, or fragments or complements thereof.

A recombinant DNA construct may contain sequences substantially similar to sequences selected from SEQ ID No. 1 and SEQ ID No. 2, or fragments or complements thereof. The dsRNAs may be expressed from multiple constructs introduced in different transformation events, or could be introduced on a single nucleic acid molecule. The dsRNAs may be expressed using a single promoter or multiple promoters. In one aspect, the invention provides a recombinant host cell having in its genome at least one recombinant DNA sequence that is transcribed to produce at least one dsRNA molecule that functions when ingested by a coleopteran pest to inhibit or reduce expression of a target gene in a pest. The dsRNA molecule may be encoded by sequences selected from SEQ ID No. 1 and SEQ ID No. 2, or fragments or complements thereof. The present invention also provides a transformed plant cell having in its genome at least one recombinant DNA sequence described herein. Transgenic plants comprising such a transformed plant cell are also provided, including progeny plants of any generation, seeds, and plant products, each comprising the recombinant DNA.

The methods and compositions of the present invention can be applied to any monocot and dicot plant, depending on the coleopteran pest control desired. Thus, the present invention provides a transformed plant with a recombinant DNA sequence as described in the sequences selected from SEQ ID No. 1 and SEQ ID No. 2, or fragments or concatemers or complements thereof, that is transcribed to produce at least one dsRNA molecule that functions when ingested by a coleopteran pest to inhibit or reduce the expression of a target gene.

The invention also provides combinations of methods and compositions for controlling coleopteran pest infestations. One means of providing a dsRNA method as described herein for protecting plants against infestation of insects is in conjunction with one or more insecticidal agents that exhibit characteristics different from those exhibited by the dsRNA methods and compositions. For example, one or more Bt proteins may be provided in the diet of insect pests in combination with one or more dsRNAs as described herein. A composition formulated for topical application or derived using a transgenic approach that combines the methods and compositions of dsRNA with Bt can be used to create synergies that were not known previously in the art for controlling insect infestation. One synergy is the reduction in the level of expression required for dsRNA (s) or the Bt protein (s). When combined, the lowest effective dose of each pest control agents can be used. It is believed that the Bt insecticidal proteins create entry pores through which the dsRNA molecules are able to penetrate more effectively into spaces remote from the gut of the insect pest, or more efficiently into the cells in the vicinity of the lesions created by the Bt proteins, thus requiring less amount of Bt or dsRNA to achieve the desired result of pesticide activity or the desired inhibition or suppression of a specific biological function in the target pest.

The present invention therefore provides a composition comprising two or more different pesticidal agents toxic to the same pest or insect species where at least one of which comprises a dsRNA described herein. In certain embodiments, the second agent may be an agent selected from the group consisting of a patatin an insecticidal protein from *Bacillus thuringiensis, Xenorhabdus* insecticidal protein, *Photorhabdus* insecticidal protein, laterosporous *Bacillus* insecticidal protein, a *Bacillus* protein *sphaericus* insecticidal, and a lignin. A *Bacillus thuringiensis* insecticidal protein can be any of a number of insecticidal proteins including, but not limited to Cry10, Cry8, Cry1, Cry35 TIC851, CryET70, Cry225 TIC901, TIC1201, TIC407, TIC417, CryET33 insecticidal protein CryET34 and binary, binary insecticidal protein CryET80 and CryET76, protein binary insecticide TICIOO and TICIOI, binary insecticide PS 149BI protein, VIP insecticidal protein TIC900 protein or the like, or combinations of the insecticidal proteins ET29 and ET37 with insecticidal protein TIC810 or TIC8 2 and insecticide chimeras of any preceding proteins.

A ribonucleic acid, which is provided in the diet, can be provided in an artificial diet formulated to meet particular nutritional requirements for particular pests. The diet can also be a recombinant cell transformed with a DNA sequence constructed for the expression of the target agent, the RNA, or the gene suppression agent. After ingestion of one or more transformed cells by the pest, a desired phenotypic result is observed, indicating that the agent is used to inhibit or reduce the expression of a target nucleotide sequence that is within the cells of the pest.

A target gene can code for the suppression of an essential protein. For the present invention the target gene is the laccase family which function is the formation of the exoskeleton. Therefore, the inhibition or reduced expression of this gene may affect essential functions for insect survival to be selected from the group apoptosis, cell differentiation and development, egg formation, larval maturation, larval stage of transition, pupation, cell division, energetic metabolism, respiration, and training and hardening of the cuticle.

Another aspect of the present invention is to provide a method for improving the yield of a plant subjected to insect pest infestation, said method comprising the steps of: a) introducing a polynucleotide comprising a sequence substantially similar to sequences selected from SEQ ID No. 1 and SEQ ID No. 2, or fragments or complements thereof or in concatemers in said plant, and b) growing the plant so as to enable the expression of said characteristic.

Yet another aspect of the invention provides agricultural products and commercially important and/or compositions of matter including, but not limited to, animal feed, commodities, products and by-products which are intended for use as food for human consumption or for use in the compositions and products intended for human consumption including, but not limited to cottonseed meal, cottonseed oil, cottonseed pellets, cottonseed lint, cottonseed fiber, cereals, and so forth. Such compositions can be defined as containing detectable amounts of a nucleotide sequence set forth herein, and, thus, are also diagnostic for any transgenic event containing such nucleotide sequences. These products are useful, at least, because they are likely to be obtained from crops propagated with fewer pesticides and organophosphates and, as a result of their incorporation of the nucleotides of the present invention for controlling the infestation of coleopteran pests in plants. Such commodities and base products can be produced from seed produced from a transgenic plant, wherein the plant expresses RNA from one or more contiguous nucleotides of the present invention or nucleotides of one or more coleopteran pests and respective complements.

A method of producing such a product comprising obtaining a plant transformed with a polynucleotide comprising a sequence selected from SEQ ID No. 1 and SEQ ID No. 2, or fragments or complements thereof or concatemer thereof, and preparation of a base product from the plant or part thereof is also provided in the present invention. In addition, a method of producing food or animal feed comprising obtaining a plant transformed with a polynucleotide comprising a sequence set forth in SEQ ID No. 1 or SEQ ID No. 2, or a fragment or concatemer or complement thereof, and preparing food or animal feed from said plant or part thereof is yet another aspect of the invention.

The invention also provides a computer readable medium having recorded therein a sequence selected from SEQ ID No. 1 and SEQ ID No. 2, or fragments or complements thereof or concatemer thereof, for use in a number of computer applications, including, but not limited to DNA identity and similarity search, protein identity and similarity search, transcription profiling characterizations, comparisons between genomes, and artificial hybridization analyzes.

In the context of this description, several terms will be used and will thus be better detailed below.

The term "nucleic acid" refers to a large molecule which can be single stranded or double stranded, composed of monomers (nucleotides) containing a sugar, a phosphate and a purine or pyrimidine base. A "nucleic acid fragment" is a fraction of a given nucleic acid molecule.

"Complementary" refers to the specific pairing of purine and pyrimidine bases that comprise nucleic acids: adenine pairs with thymine and guanine pairs with cytosine. Then, the "complement" of a first nucleic acid fragment refers to a second nucleic acid fragment whose sequence of nucleotides is complementary to the first nucleotide sequence.

In most developed plants, deoxyribonucleic acid (DNA) is the genetic material while ribonucleic acid (RNA) is involved in the transfer of information from DNA into proteins. A "genome" is the entire main body of genetic material contained in each cell of an organism. The term "nucleotide sequence" refers to nucleotide sequences polymers, forming a strand of DNA or RNA which can be single- or double-stranded, optionally synthetic, non-natural or altered nucleotide bases capable of incorporation into of DNA or RNA polymers. The term "oligomer" refers to short nucleotide sequences, usually up to 100 bases in length. The term "homologous" refers to the connection between the nucleotide sequences of two nucleic acid molecules or between the amino acid sequences of two protein molecules. The estimate of such homology is provided by hybridization DNA-DNA or RNA-RNA under stringent conditions as defined in the art (as mentioned in document US20030074685, Hames and Higgins Ed. (1985) Nucleic Acid Hybridization, IRL Press, Oxford, UK; or by the comparison of sequence similarity between two nucleic acid molecules or protein (as mentioned in the document US20030074685, Needleman et al, J Mol. Biol. (1970) 48: . . . 443-453).

"Gene" refers to nucleotide fragment that expresses a specific protein, including preceding regulatory sequences (5' untranslated region) and posterior regulatory sequences (3' untranslated region) to the coding region. "Native gene" refers to an isolated gene with its own regulatory sequence found in nature. "Chimeric gene" refers to the gene comprising encoding, heterogeneous and regulatory sequences not found in nature. The chimeric gene of the present invention comprises isolated nucleic acid molecules in sense or antisense orientation, operably linked to active promoters. Gene constructs of the present invention may contain one or more chimeric genes and may or may not have introns. "Endogenous gene" refers to the native gene normally found in its natural location in the genome and is not isolated. "Exogenous gene" refers to a gene not normally found in the host organism but that is introduced by gene transfer. "Pseudogene" refers to a nucleotide sequence that does not encode a functional enzyme.

"Coding sequence" refers to a DNA sequence which encodes a specific protein and excludes the non-coding sequence. "Interrupted coding sequence" means that the sequence acts as a separator (for example, one or more introns connected via joints). An "intron" is a nucleotide sequence that is transcribed and is present in the pre mRNA, but is removed through cleavage and re-binding of the mRNA within the cell generating a mature mRNA that can be translated into a protein. Examples of introns include, but are not limited to, PDK2 intron, catalase intron from the castor bean, cotton intron Delta 12 desaturase, delta 12 desaturase from *Arabidopsis*, ubiquitin intron from maize, the SV40 intron, the introns of the malate synthase gene.

"RNA transcript" refers to the transcription product resulting from catalyzed transcription by RNA polymerase of a DNA sequence. When the RNA transcript is a perfect copy of the DNA sequence, it is referred to as the primary transcript or it may be a RNA sequence derived from post-transcriptional process of the primary transcript and is then referred to as the mature transcript. "Messenger RNA (mRNA)" refers to the RNA that lacks introns. "Sense RNA" refers to a RNA transcript that includes the mRNA. "Antisense RNA" refers to a RNA transcript that is complementary to all parts of a primary transcript or mRNA and which can block expression of a target gene by interfering in the processing, transport and/or translation of its primary transcript or mRNA. The complementarity of an antisense RNA may be with any part of the specific gene transcript, that is, 5' untranslated sequence, 3' untranslated sequence, introns or the coding sequence. Moreover, antisense RNA may contain regions of ribozyme sequences that increase the efficacy of antisense RNA to block the gene expression. "Ribozyme" refers to the catalytic RNA and includes sequence-specific endoribonucleases. "DsRNA (double-stranded)" refers to the hairpin structure formed between the mRNA sequence or RNA sense, the sequence of a spacing region and the antisense RNA sequence. "Spacing region" refers to nucleotide sequence which is unrelated to the target gene sequence such as an intron sequence.

The term "vector" refers to a replicon, such as plasmid, phage or virus into which other genetic sequences or elements (be it DNA or RNA) can be connected. Thus, genes can be replicated together with the vector. The term "recombinant vector" is a result of the combination of a commercial vector nucleic acid molecules of the invention operably linked to a promoter of interest and a termination signal. Such vectors may be obtained commercially, including those supplied by Clontech Laboratories, Inc. (Palo Alto, Calif.), Stratagene (La Jolla, Calif.), Invitrogen (Carlsbad, Calif.), New England Biolabs (Beverly, Mass.) and Promega (Madison, Wis.). Examples of vectors used in the present invention, but are not limited to, are the vectors of the series pCambia (Bioforge Co.), pBI121 (Chen, Po-Yen; Wang, Chen Kuen; Soong, Shaw Ching; To Kin Ying. Complete sequence of the binary vector pBI121 and its application in cloning T-DNA insertion from transgenic plants. Molecular Breeding vol. 11 issue 4 May 2003. p. 287-293), pBSK (Addgene Co.), pGEM-T easy (Promega Corporation), pET101/D-TOPO (Invitrogen). Obtaining recombinant vectors comprising promoters linked to nucleic acids are known in the art and can be found in Sambrook et al. (Sambrook, J., Russell, D. W., Molecular Cloning, A Laboratory Manual, 2nd ed., Cold Spring Harbor Laboratory Press. 1989).

"Substantially similar" or "substantial similarity" refers to nucleic acid fragments wherein changes in one or more nucleotide bases do not affect the ability of the nucleic acid fragment to mediate alteration of gene expression by gene silencing via, for example, the antisense technology, co-suppression or RNA interference (RNAi). Substantially similar nucleic acid fragments of the present invention can also be characterized by the percent similarity of their sequences of nucleotides with the nucleotide sequences of nucleic acid fragments described herein (SEQ ID No. 1 and SEQ ID No. 2), as determined by common algorithms employed in the art. Preferred nucleic acid fragments are those whose nucleotide sequences have at least about 40 or 45% sequence identity, preferably about 50% or 55% sequence identity, more preferably about 60% or 65% identity sequence, more preferably about 70% or 75% sequence identity, more preferably about 80% or 85% sequence identity, most preferably about 90%, 91%, 92%, 93%, 94%, 95%, 96%, 97%, 98% or 99% sequence identity compared to a reference sequence. The sequence alignment and the calculation of percentage similarity of the present invention were made using the DNAMAN software for Windows (Lynnon Corporation, 2001), using sequences deposited in Gene Bank, through the Web browser integration.

One way to form the dsRNA is being present in the DNA molecule the target gene nucleotide sequence in the sense orientation, and a nucleotide sequence in antisense orientation, and there may be or not a spacing region between the sense and antisense nucleotide sequences. Said nucleotide sequences may be comprised of from about 19 nt to 2000 nt or about 5000 or more nucleotides, each having a substantial overall sequence similarity of about 40% to 100%. The longer the sequence, the less stringence is required for full substantial sequence similarity. The fragments containing at least about 19 nucleotides should be preferably about 90%, 91%, 92%, 93%, 94%, 95%, 96%, 97%, 98% or 99% of the sequence identity when compared to the reference sequence, with the possibility of having about 2 distinct non-contiguous nucleotides. Preferably, one uses fragments above 60 pb, more preferably fragments ranging from 100 to 500 pb.

In one of the aspects of the invention, the dsRNA molecule may comprise one or more regions having a substantial sequence similarity for the regions with at least about 19 consecutive nucleotides of the sense nucleotides of the target gene, defined as first region and one or more regions having a substantial sequence similarity for the regions with about 19 consecutive nucleotides of the complement of the sense nucleotides of the target gene, defined as second region, wherein these regions may have pairs of bases separating them one from each other.

Conveniently, the dsRNA (Double-stranded RNA) as described may be introduced into the host cells by introducing and possibly integrating a gen construct containing the nucleic acid molecules of the present invention, transition thereof for producing the dsRNA. Therefore, in another embodiment, the invention is also supported by having a gen construct that is capable of being expressed in cells of eukaryotic organisms of interest, operatively linked to a DNA molecule that, when transcribed, produces a dsRNA molecule comprising a first region and a second region, wherein:

(a) the first region comprises a nucleotide sequence of at least about 19 consecutive nucleotides having a substantial sequence similarity with at least about 19 consecutive nucleotides of the sequence of sense nucleotides of the target gene;

(b) the second region comprises a nucleotide sequence of about at least 19 consecutive nucleotides having a substantial sequence similarity with the complement of about at least 19 consecutive nucleotides of the sequence of sense nucleotides of the target gene;

(c) the first and the second region are capable of forming a double-stranded RNA, which may have, in addition to the total length of the first and of the second region, a spacing region between them containing at least about 19 nucleotides.

"Promoter" refers to the DNA sequence in which the gene, usually located upstream of the coding sequence, which controls the expression of the coding sequence promoting recognizance by the polymerase RNA and other factors required for the transcription itself. In an artificial DNA construct, promoters may also be used for transcribing dsRNA. Promoters may also contain DNA sequences that are involved in linking protein factors, which control the effect of the transition start in response to physiological or development conditions.

In one of the aspects of the invention, the promoter is a constitutive promoter. Ion another aspect of the invention, the promoter activity is stimulated by external or internal factors, such as, but not limited to hormones, chemical compounds, mechanical impulses, and conditions of biotic or abiotic stress. The promoter activity may also be regulated in a time-and-space way (as for example, tissue-specific promoters and regulation promoters during the development).

A promoter may contain enhancers. An enhancer is a DNA sequence that may stimulate the promoter activity. It may be a innate element of the promoter or a heterologous element inserted to increase the level and/or the tissue-specificity of a promoter. "Constructive promoters" refer to those that direct the gene expression in all the tissues and all the time. "Tissue-specific" promoters or "development-specific" promoter are those that direct the gene expression almost exclusively in specific tissues, such as leaves, roots, stems, flower, fruits or seeds, or in specific stages of the development in a tissue, as in the beginning or at the end of embryogenesis. The term "expression" refers to transcription and stable accumulation of the dsRNA derived from the fragments of nucleic acids of the invention, which, in conjunction with the apparatus of production of the cell protein, results in altered levels of mio-inositol 1-phostate synthase. "Inhibition by interference" refers to the production of dsRNA transcripts capable of preventing the expression of the target protein. "Suitable regulation sequences" refer to the nucleotide sequences in native or chimeric genes, which are located above (non-translated region 5'), within, and/or below (non-translated region 3') of the fragments of nucleic acid of the invention, which control the expression of fragments of nucleic acid of the invention.

"Altered levels" refer to the production of gene product in transgenic organisms in amounts or proportions that differ from those in normal or non-transgenic organisms. The present invention also reports vectors, which include sequences of the gene of the enzyme laccase in the sense and antisense orientation, and host cells which are genetically engineered with vectors of the invention. "Transformation" refers to the transfer of the exogenous gene into the genome of a host organism and a genetically stable heritage.

"Plants" refer to photosynthetic organisms, both eukaryotic and prokaryotic, wherein the term "developed plants" refers to eukaryotic plants. The nucleic acids of the invention may be used for imparting desires features in essentially any plant. Then, the invention has use on various species of plants, including species of the genera: *Anacardium, Anona, Arachis, Artocarpus, Asparagus, Atropa, Avena, Brassica, Carica, Citrus, Citrullus, Capsicum, Carthamus, Cocos, Coffea, Cucumis, Cucurbita, Daucus, Elaeis, Fragaria, Glycine, Gossypium, Helianthus, Heterocallis, Hordeum, Hyoseyamus, Lactuca, Linum, Lolium, Lupinus, Lycopersicon, Malus, Manihot, Majorana, Medicago, Nicotiana, Olea, Oryza, Panieum, Pannesetum, Passiflora, Persea, Phaseolus, Pistachia, Pisum, Pyrus, Prunus, Psidium, Raphanus, Ricinus, Secale, Senecio, Sinapis, Solanum, Sorghum, Theobromus, Trigonella, Triticum, Vicia, Vitis, Vigna,* and *Zea*.

In one of the aspects of the invention, the promoter is one expressed ion plants. As used herein, the term "promoter expressed in plants" means a DNA sequence that is capable of initiating and/or controlling transition in a plant cell. This includes any promoter of vegetable origin; any promoter of non-vegetable origin that is capable of directing the expression of a vegetable cell, for example, promoters of viral or bacterial origin such as CaMV35S (as mentioned in patent application US20030175783, Hapster et al, 1988 Mol. Gen. Genet. 212, 182-190) and promoters of the gene present in the T-DNA of Agrobaterium; tissue-specific or organ-specific promoters, including, but not limited to seed-specific promoters, (WO8903887), organ-primordia-specific promoters (as mentioned in patent application US20030175783, An et al., 1996 The Plant Cell 8, 15-30), stem-specific promoters (as mentioned in patent application US20030175783, Keller et al., 1988 EMBO J. 7: 3625-3633), leaf-specific promoters (as mentioned in patent application US20030175783, Hudspeth et al., 1989 Plant Mol Biol 12:579-589), mesophyle-specific promoters, root-specific promoters (as mentioned in patent application US20030175783, Keller et al., 1989 Genes Devel. 3:1639-1646), tuber-specific promoters (as mentioned in patent application US20030175783, Keil et al., 1989 EMBO J. 8: 1323:1330), vascular-tissue-specific promoters (a mentioned in patent application US20030175783, Peleman et al., 1989 Gene 84: 359-369), stamen-specific promoters (WO8910396, WO9213956), dehiscence zone-specific promoter (WO9713865); and the like.

The termination signal of the transcription and the polyadenylation region of the present invention includes, but is not limited to SV40 termination signal, HSV TK adenilation signal, termination signal of the gene of nopalin synthase of *Agrobacterium tumefasciens* (nos), termination signal of the gene RNA 35S do CaMV, termination signal of the virus that attacks *Trifolium subterranean* (SCSV), termination signal of the gene trpC of *Aspergillus nidulans*, and other similar ones.

The present invention also includes providing dsRNA molecules, which can be obtained by transcribing the molecules contained in the gen constructions and that are useful to the methods according to the invention.

Another objective of the present invention is to provide eukaryotic cells and eukaryotic organisms containing dsRNA molecules of the invention, or containing the chimeric gene or the gene constructs capable of producing dsRNA molecules of the invention. The gene constructs may be stably integrated in the genome of the cells of organisms.

In another aspect of the invention, the gene constructs may be provided in a DNA molecule capable of replicating in an autonomous manner in the cells of eukaryotic organisms, such as viral vectors. The gene construction or dsRNA may also be arranged in a transient way in the cells of eukaryotic organisms.

The gene constructs or chimeric gene of the invention may also be introduced into the genome of the desired host plant through a number of conventional techniques. For instance, it can be introduced directly into the gene DNA of the vegetable cell by using techniques such as electroporation and microinjection of protoplasts of plant cells, or the construct may be introduced directly into the vegetable tissue by using ballistic methods, such as bombardment of particles covered with DNA.

Microinjection techniques are known from the prior art and well described in scientific and patent literature. The introduction of gene constructs by using precipitations of polyethylene glycol is described in Paszkowski et al. Embo J. 3:2717-2722, 1984 (as mentioned in patent application US20020152501). Electroporation techniques are described in From et al. Proc. Natl. Acad. Sci. USA 82:5824, 1985 (as mentioned in patent application US20020152501). Ballistic transformation techniques are described in Klein et al. Nature 327:70-73, 1987 (as mentioned in patent application US20020152501).

Alternatively, the gene constructs may be combined with suitable T-DNA flanking regions and introduced into the host conventional vector *Agrobacterium tumefasciens*. The virulence function of the host *Agrobacterium tumefasciens* will direct the insertion of the gene constructs and adjacent mark into the DNA of the vegetable cell when the cell is infected by the bacterium. Transformation techniques mediated by *Agrobacterium tumefasciens*, including disarmament and the use of binary vectors, are well described in the scientific (as mentioned in patent application US 20020152501, Horsch et al. Science 233:496-498, 1984; and Fraley et al. Proc. Natl. Acad. Sci. USA 80:4803, 1983).

Transformed plant cells that are derived from any of the transformation techniques described above may be cultivated for regenerating the whole plant that has the transformed genotype and then the desired phenotype such as expression of a molecule that causes absence or reduction of the formation of the exoskeleton of coleopterous insects. Such regeneration techniques rely on the handling of certain phytohomones in a medium for growing tissue culture, typically containing a biocidal and/or herbicidal marker, which should be introduced together with the desired sequence of nucleotide sequence. Regeneration of plants from protoplast culture is described in Evans et al., Protoplasts Isolation and Culture, Handbook of Plant Cell Culture, pp. 124-176, MacMillilan Publishing Company, New York, 1983; and Binding, Regeneration of Plants, Plant Protoplasts, pp. 21-73, CRC Press, Boca Raton, 1985 (as mentioned in patent application US20020152501). Regeneration may also be obtained through calli of plant, explants, organs, or part thereof. Tais técnicas de regeneração são descritas geralmente em Klee et al., Ann. Ver. Of Plant Phys. 38:467-486, 1987 1985 (as mentioned in patent application US20020152501).

Without restricting the invention to a particular action mode, one expects that the enzyme in eukaryotic cells responsible for generating small RNA molecules with about 21 dsRNA nucleotides (like DICER IN *Drosophila*) can be saturated by including an excess of dsRNA sequences (that is, complementary RNA molecules) which are related to the sequence of nucleotides of the target gene or of the gene to be silenced.

The natural variation in the subsequent regulation of the expression of the target gene occurring between different lines of eukaryotic organism, comprising the same dsRNA molecule will be replaced by handling the gene silencing spectrum.

The embodiments of the present invention may be effective against a number of pests. For the purposes of the present invention, the pests include, but are not limited to insects, fungi, bacteria, nematodes, mites, protozoan pathogens, animal parasites, and the like. Pests of particular interest are insect pests, particularly insect pests that cause significant damages to agricultural plants. By "insect pests" one understands insects and other similar pests such as the insects from the orders: Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, etc., particularly Coleoptera, specially *Anthonomus grandis, Diabrotica virgifera, Tenebrio molitor, Tribolium castaneum, Phoracantha semipunctata, Lixus angustatus, Acanthoscelides obtectus* and other coleoptera that cause damages to woods and agronomically important plants of the families Scolytidae, Cerambycidae, Curculionidae and Bostrichida. Insect pests of the present invention of most cultivar include, but are not limited to: corn-plant—*Ostrinia nubilalis, Agrotis ipsilon, Helicoverpa zea, Spodoptera frugiperda, Diatraea grandiosella, Elasmopalpus lignosellus, Diatraea saccharalis, Diabrotica virgifera virgifera, Diabrotica longicornis barberi, Diabrotica undecimpunctata howardi, Melanotus* spp., *Cyclocephala borealis, Cyclocephala immaculata, Popillia japonica, Chaetocnema pulicaria, Sphenophorus maidis, Rhopalosiphum maidis, Anuraphis maidiradicis, Blissus leucopterus leucopterus, Melanoplus femurrubrum, Melanoplus sanguinipes, Hylemya platura, Agromyza parvicornis, Anaphothrips obscrurus, Solenopsis milesta, Tetranychus urticae*; Sorgo—*Chilo partellus, Spodoptera frugiperda, Helicoverpa zea, Elasmopalpus lignosellus, Feltia subterranea, Phyllophaga crinita, Eleodes, Conoderus,* and *Aeolus* spp., *Oulema melanopus, Chaetocnema pulicaria, Sphenophorus maidis, Rhopalosiphum maidis, Sipha flava, Blissus leucopterus leucopterus, Contarinia sorghicola, Tetranychus cinnabarinus, Tetranychus urticae*; Wheat—*Pseudaletia unipuncata, Spodoptera frugiperda, Elasmopalpus lignosellus, Agrotis orthogonia, Elasmopalpus lignosellus, Oulema melanopus, Hypera punctata, Diabrotica undecimpunctata howardi, Schizaphis graminum, Macrosiphum avenae, Melanoplus femurrubrum, Melanoplus differentialis, Melanoplus sanguinipes, Mayetiola destructor, Sitodiplosis mosellana, Meromyza americana, Hylemya coarctata, Frankliniella fusca, Cephus cinctus, Aceria tulipae*; Sunflower—*Cylindrocupturus adspersus, Smicronyx fulus, Smicronyx sordidus, Suleima helianthana, Homoeosoma electellum, Zygogramma exclamationis, Bothyrus gibbosus, Neolasioptera murtfeldtiana*; Cotton—*Heliothis virescens*, apple-caterpillar; *Helicoverpa zea*, ear-of-corn caterpillar; *Spodoptera exigua, Spodoptera frugiperda* caterpillar; *Pectinophora gossypiella*, pink-bollworm; *Anthonomus grandis*, boll-weevil; *Aphis gossypii*, cotton-plant louse; *Pseudatomoscelis seriatus*, cotton leaping flea; *Trialeurodes abutilonea*, white fly *Bemisia tabaci; Melanoplus femurrubrum*, grasshopper; *Melanoplus differentialis*, grasshopper; *Thrips tabaci*, tobacco *Thrips; Franklinkiella fusca*, tripes; *Tetranychus cinnabarinus*, red mite; *Tetranychus urticae*, acaro-rajado; Rice—*Diatraea saccharalis, Spodoptera frugiperda, Helicoverpa zea, Colaspis brunnea, Lissorhoptrus oryzophilus, Sitophilus oryzae, Nephotettix nigropictus, Blissus leucopterus leucopterus, Acrosternum hilare*; Soybean—*Pseudoplusia includens, Anticarsia gemmatalis, Plathypena scabra, Ostrinia nubilalis, Agrotis ipsilon, Spodoptera exigua, Heliothis virescens, Helicoverpa zea, Epilachna varivestis, Myzus persicae, Empoasca fabae, Acrosternum hilare, Melanoplus femurrubrum, Melanoplus differentialis, Hylemya platura, Sericothrips variabilis, Thrips tabaci, Tetranychus turkestani, Tetranychus urticae*; Barley—*Ostrinia nubilalis, Agrotis ipsilon, Schizaphis graminum, Blissus leucopterus leucopterus; Acrosternum hilare, Euschistus servus, Jylemya platura, Mayetiola destructor, Petrobia latens*; Canola—*Vrevicoryne brassicae, Phyllotreta cruciferae, Phyllotreta striolata, Phyllotreta nemorum, Meligethes aeneus, Meligethes rufimanus, Meligethes nigrescens, Meligethes canadianus,* and *Meligethes viridescens*; Potato—*Leptinotarsa decemlineata*.

EXAMPLES

The present invention is also defined by the following examples. One should bear in mind that these Examples, while indicate part of the invention, are intended for visualization purposes only and therefore do not have limit the scope of the instant inventions.

Usual Molecular Biology techniques such as transformation of bacteria and electrophoresis into agarose gel of nucleic acids are referred to by common terms to describe them. Details about said techniques, well known in the art, can be found in Sambrook, et al. (Molecular Cloning, A. Laboratory Manual, $2^{nd}$ ed., 1989, Cold Spring Harbor Laboratory Press). Several solutions utilized in experimental manipulation are referred to as their common names such as "lysis solution", "SSC", "SDS" etc. The compositions of said solutions can be found in the above-mentioned reference Sambrook, et al.

Example 1

Synthesis of dsRNA of Laccase 2 of *Anthonomus grandis*

Figure 4:
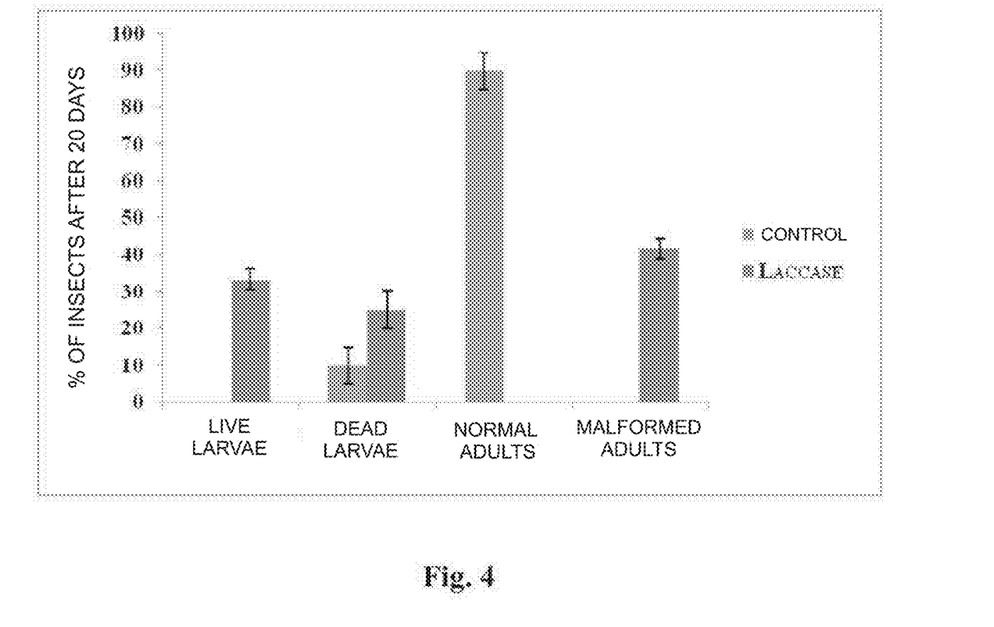
FIG. 4—Assessment of dsRNA effect lacase2 20 days after microinjection. In red, experiment with dsRNA lacase2; and in blue, control experiments, with double distilled H20.

Eggs, larvae and adult insects of *A. grandis* were created in the Embrapa Genetic Resources and Biotechnology Laboratory of Bioecology Semiochemicals of Insects, in Brasilia-DF. The colony was fed with artificial diet as described by Monnerat and colleagues (MONNERAT, R. G. et al. "*Criação massal do bicudo do algodoeiro Anthonomus grandis em laboratório*". Technical Release—Embrapa Genetic Resources and Biotechnology, vol. 46, p. 4, 2000. MONNERAT, R. G. et al. "*Parâmetros bionômicos do bicudo do algodoeiro* (*Anthonomus grandis*) *criado em dieta artificial para a realização de bioensaios*". Embrapa Genetic Resources and Biotechnology—Bulletin of Research and Development, vol. 29, p. 20, 2002) and maintained at 26+2° C., relative humidity of 60±10% and photophase of 12 hours.

For cloning and sequencing of a fragment of laccase 2 of *A. grandis,* total RNA was extracted from eggs, larvae and adult insects using Trizol (Invitrogen) following the protocol indicated by the manufacturer. cDNA was synthesized from 5 µg of the total RNA using the Superscript II TM First-Strand Synthesis System for RT-PCR kit (Invitrogen) using oligo d(T)-AP. For the initial amplification of the fragment of Laccase 2, primers designed from the sequence obtained from the *A. grandis* transcriptome database, corresponding to a region of the copper binding site of laccase 2, were utilized. The primer sequences were 5'GCTCCGCTTCTATCTCAGT3' (SEQ ID NO: 3) and 5'GCAATGGTGTCTTTACCG3' (SEQ ID NO: 4) for the direct and reverse primer, respectively. A polymerase chain reaction (PCR) was performed under the following conditions: 94° C. for 1 min, annealing temperature of 60° C. and extension at 72° C. for 1 minute for 30 cycles.

For the synthesis of double-stranded RNA, the fragment of 332 bp amplified and sequenced [SEQ ID NO: 2] was used as template. The software BLOCK-iT™ RNAi Designer (available at rnaidesigner.invitrogen.com/rnaiexpress) was used to analyze the sequence of 332 pb and display regions most likely to be used in gene silencing.

The double-stranded RNAs were synthesized from the product of the PCR of 332 bp flanked by the minimal sequence of the T7 promoter. The product of the PCR was cloned and sequenced for assessment of the sequence.

After confirmation of the sequence, the synthesis of dsRNA was carried out using 0.5 µg of the product of the PCR as a template for a transcription reaction volume of 20 µL, as described in the user's book of the MEGAscript® T7 High Yield (Ambion) kit.

The reaction was incubated for 16 hours at 37° C. followed by treatment with DNAse I for 15 minutes. To align the double-stranded RNA, the reaction products were incubated at 70° C. for 5 minutes and cooled at room temperature (22° C.). For purification of the transcription product, an extraction was performed with phenol/chloroform and subsequent precipitation with isopropyl alcohol, according to the protocol described by the manufacturer of the MEGAscript® T7 High Yield (Ambion) kit. The dsRNA was dissolved in DEPC-treated water and after quantification by spectrophotometry, the determined amount was 4 µg of dsRNA.

Example 2

Bioassays on Microinjection of dsRNA and Evaluation of the Silencing of the Gene Encoding Laccase 2 in *A. grandis*

A cDNA sequence of the Laccase 2 gene in the transcriptome of *Anthonomus grandis*, which size was 1817 pb (SEQ ID NO: 1), was identified. Within this sequence we selected a region of 332 pb (SEQ ID No. 2) to serve as a template for the synthesis of dsRNA molecules, as described in Example 1. This dsRNA was utilized in microinjection assays and the effects of the silencing were evaluated by morphological analysis, mortality and reduced expression levels of the laccase 2 gene by real time PCR.

Morphological Analysis and Mortality

The bioassay on boll weevil was performed by microinjection of dsRNA. Larvae were weighed so that only individuals weighing between 30 and 40 mg were used. In each test, 1 µL containing 500 ng of dsRNA was injected into the dorsal region of 3rd instar larvae, and measures were taken not to damage their dorsal artery. A Gas tight (Hamilton Co.) Luer lock (LT) 1701 LT model, 10 pL volume, 51 mm needle, gauge 26S, point style 4 and 12° bevel microsyringe was used for microinjection. Twenty weevil larvae underwent microinjection and were kept on an artificial diet maintained at 26±2° C., relative humidity of 60±10% and photophase of 12 hours. A morphological evaluation was carried out over time up to 60 days after injection. This experiment was repeated three times, at different times. In this experiment, 20 days after microinjection insects managed to enter the pupal stage, but development was abnormal, generating a pupa/adult hybrid (FIG. 1*b, c, d*) with malformed cuticula full abnormal protrusions (FIG. 1*a*) and lighter color. However, most of these deformed insects were dead when analyzed and none of the insects came to adulthood, with no survivors 25 days after microinjection.

In the same experiment, it was observed that 20 days after microinjection, some insects were still in the larval stage, alive and feeding. However, on the $30^{th}$ day, all those larvae were dead. Lipid accumulation that occurs normally in the last instar of the larval stage showed that the larva continued to feed after microinjection (FIG. 2*b*). This accumulation of lipids works as an energy storage for the pupal stage that does not feed. However, as these larvae did not enter the pupal stage, their appearance is of "stuffed" larvae since apparently there was no growth of the cuticle following the increase in body volume (FIG. 2*b, d*). Structures that are similar to the adult females' ovipositor or to the male's aedeagus (copulatory organ) appear in these larvae (FIG. 2*e, f*).

FIG. 3 shows a scheme of the weevil life cycle with a summary of what happened in the experiments on a time-basis. In a cycle of about 30 days, the weevil was microinjected around the 18th day (FIG. 3, blue arrow). Observed on the 20th day after microinjection, about the 50th day in the cycle (FIG. 3, red arrow), the three bioassay experiments, with 20 larvae each, revealed the result seen in FIG. 4. Approximately 10% of the larvae microinjected with H2O (control) and 25% of the ones microinjected with dsRNA probably died by manipulation. The remaining larvae of the control experiment (90%) reached adult stage and the plate was filled with eggs and some recent larvae, showing that the injection with H2O apparently did not affect the reproduction of the insects. larvae microinjected with dsRNA of laccase 2, 33% were still larvae and 42% managed to continue the cycle (FIG. 4), but stopped sometime between pupa and adulthood, but by the time the analysis was carried out they were already dead.

Analysis on the Expression Levels of the Laccase 2 Gene after Microinjection with dsRNA of Laccase 2

Bioassays on microinjection of dsRNA of laccase 2 were performed as previously described for extraction of total RNA and subsequent analysis by qRT-PCR. Larvae microinjected with dsRNA of laccase2 or H2O were collected 20 days after microinjection. Malformed Pupae/adults were collected 14 days after microinjection. cDNA synthesis was performed using the Superscript III™ First-Strand Synthesis SuperMix for qRT-PCR kit (Invitrogen) in accordance with the manufacturer's instructions. For cDNA synthesis, total RNA was extracted from larvae and adults crushed in a mortar containing liquid N2, using Trizol reagent (Invitrogen Life Technologies) according to manufacturer's instructions. The samples were treated with 2 U of RNase-free DNase I (Ambion, Invitrogen Life Sciences) for 30 minutes at 37° C. according to the manufacturer's instructions. After the column based clean up step of the RNeasy Micro Kit (QIAGEN) and after the quality of the sample in 1.5% agarose gel is checked, cDNA synthesis was performed using the Superscript III™ First-Strand Synthesis SuperMix kit for qRT-PCR (Invitrogen) from 500 ng of RNA, following the manufacturer's instructions.

To perform the qRT-PCR, the Fast 7500 thermocycler (Applied Biosystems, USA) was used with specific primers for each gene (Table 7). Each reaction was performed in a final volume of 10 µL, 2.5 µL of which being SYBR Green Rox Plus PCR Mix (LGC Biotechnology), 2 µl being cDNA diluted 40 times, 4.7 µl of bi-distilled H2O and 0.4 µl of each primer (0.2 µM direct and reverse). The reaction took place at 95° C. for 10 minutes, followed by 40 cycles of incubations at 95° C. for 15 s and 60° C. for 1 min. At the end of the 40 cycles a dissociation curve for each amplified fragment (60-94° C., each 0.5° C. for 1 sec.) was performed to verify the possible formation of primer dimers or sample contamination. The qRT-PCR reactions were performed in triplicate, and negative controls containing water instead of cDNA were included to verify contamination in the samples. A negative control containing total RNA was performed to ensure the absence of genomic DNA. Expression levels were determined as the number of cycles required to reach a fixed threshold in the exponential phase of the PCR. The number of cycles was referred to as the Cq (quantification cycle) value, replacing former Ct (threshold cycle) or Cp (crossing point), according to RDML standards (Lefever et al., 2009). The efficiency of each primer to each reaction and Cqs were individually calculated from with the aid of the qPCR miner software (www.miner.ewindup.info) (ZHAO; Fernald, 2005).

Figure 5:
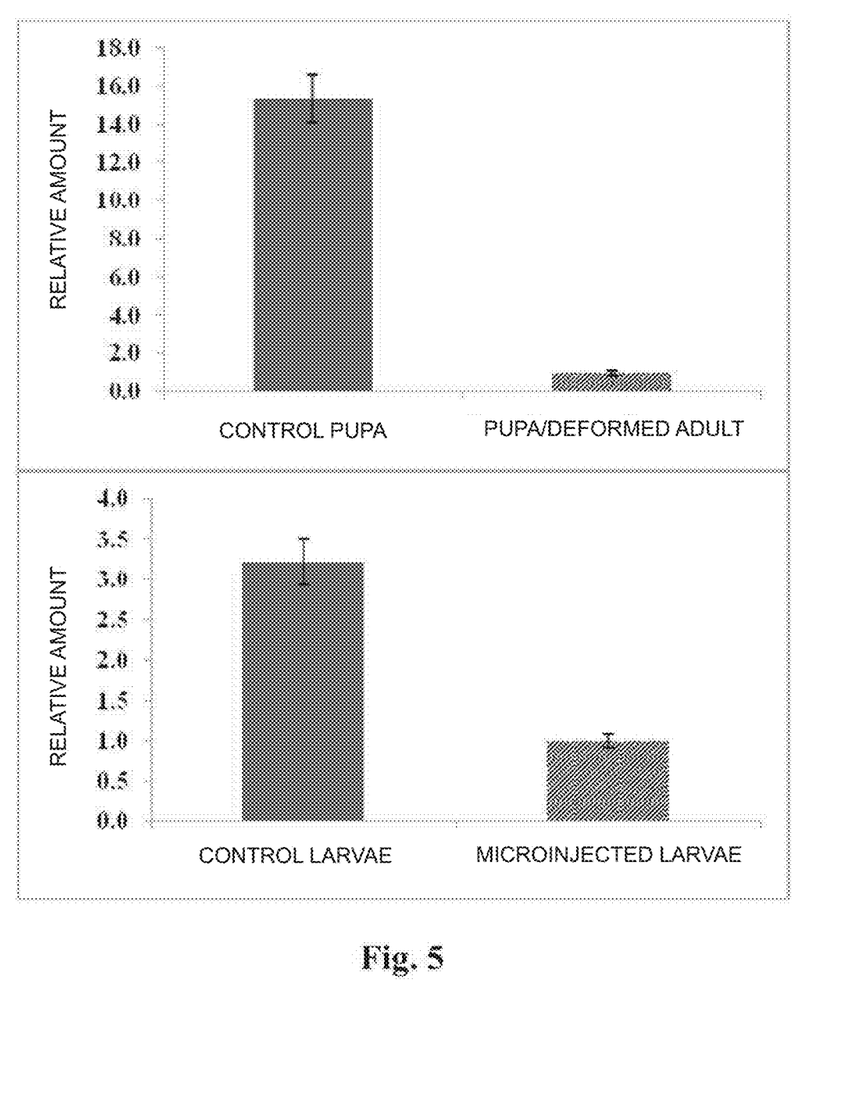
FIG. 5—Comparison of the amount of lacase2 transcripts between insect control and the pupae/adults (A) or larvae (B) after microinjection with dsRNA. The reference genes used were GAPDH and β-tubulin.

From the results obtained from the bioassays, an analysis on the relative expression of the laccase 2A was carried out by qRT-PCR on the two types of insects found 20 days after microinjection. Deformed pupae/adults had to be collected earlier (14 days after microinjection), since it was difficult to find individuals alive on the 20th day. The expression of the laccase 2A gene in them was decreased about 15-fold (FIG. 5A) compared to the same gene expression in pupae from larvae microinjected with H2O. The laccase 2A gene was about 3 times less expressed in the larvae microinjected with dsRNA and that remained alive after 20 days (FIG. 5B).

These results indicate an effect on the formation and sclerotization of the insect's cuticula, since the laccase 2A gene is expressed in subcuticular epithelial cells, when a new cuticula is formed and sclerotization occurs, as in cases of molt.

Figure 1:
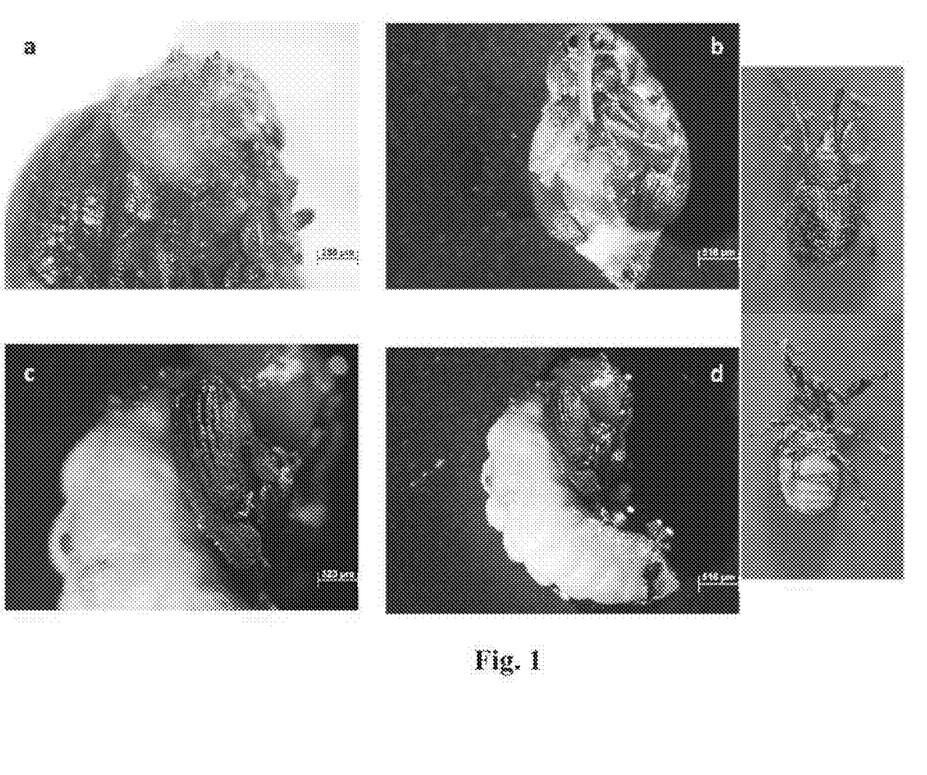
FIG. 1—pupae/adults observed 20 days after microinjection of dsRNA lacase2A. It is possible to notice a malformation and low pigmentation in the head cuticle (a) and deformation of the body, and the maintenance of a larval pupo-phenotype (b, c, d) when compared with normal adults (right).
Figure 2:
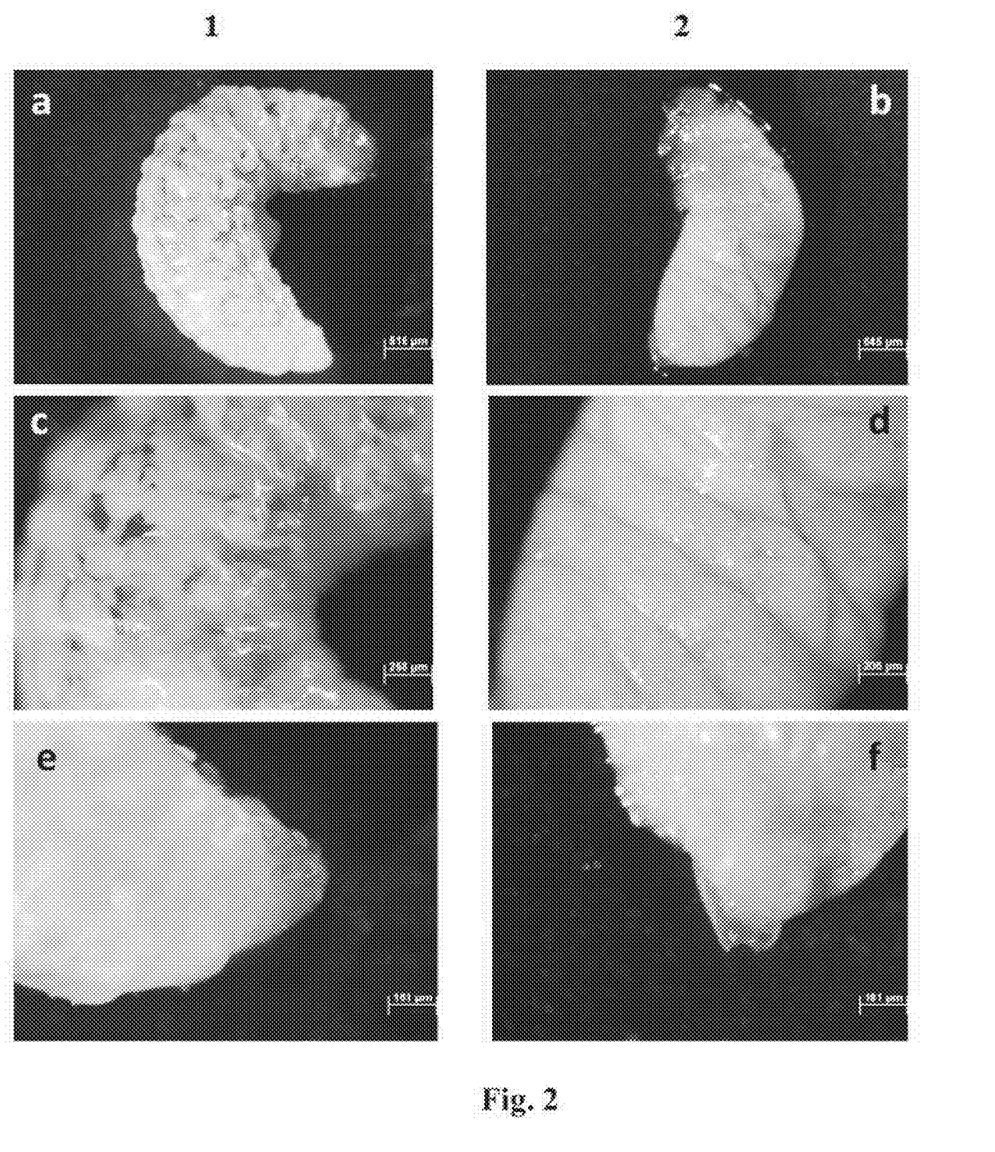
FIG. 2—Comparison between normal larvae of 3rd instar (1-a, c, e) and larvae observed 20th day after microinjection dsRNA lacase2A (2-b, d, f). In F, it is possible to observe a structure formation which may be a ovipositor or aedeago, this structure only in normal adults.
Figure 3:
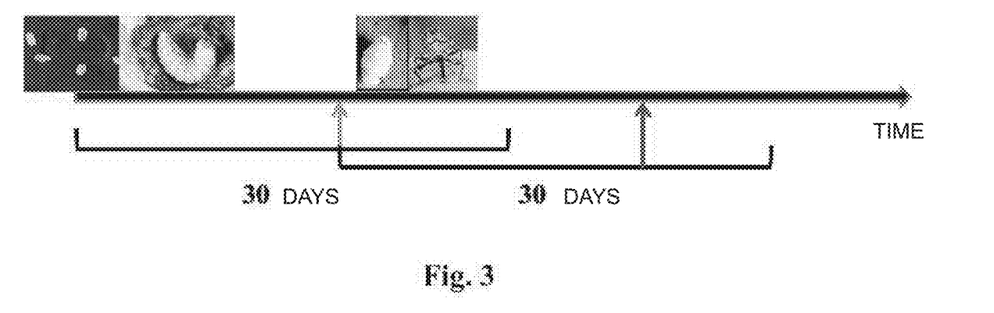
FIG. 3—Scheme of bioassay with boll weevil dsRNA laccase 2 during the insect's life cycle. The blue arrow indicates the time of microinjection and the red arrow, the time when the effects were observed. For more information, see the text.

As for the phenotype, the development of microinjected 3rd instar larvae has gone through some changes. Variation in said phenotype was noticed. Some of the larvae failed to continue its development, remaining as larvae for a longer time, causing their death. Some larvae managed to enter the pupal stage. However, these have not reached adulthood and exhibited malformations in their exoskeleton (FIG. 2).

The invention claimed is:

1. An isolated double-stranded ribonucleic acid (dsRNA) molecule, wherein said dsRNA molecule comprises a first ribonucleotide sequence at least 90% identical to a sequence entirely complementary to 60 or more contiguous nucleotides of SEQ ID NO: 1 or 2, said first ribonucleotide sequence being present on one strand of said dsRNA,
   wherein said dsRNA molecule further comprises a second ribonucleotide sequence entirely complementary to said first ribonucleotide sequence, said second ribonucleotide sequence being present on the other strand of said dsRNA, and
   wherein said dsRNA molecule, when assimilated by a coleopterous pest of plants, inhibits or reduces the proliferation of said pest.

2. The isolated ribonucleic acid molecule according to claim 1, wherein said first ribonucleotide sequence is entirely complementary to at least 60 contiguous nucleotides of a sequence selected from the group consisting of SEQ ID NO: 1 or 2.

3. A polynucleotide
   encoding the dsRNA molecule of claim 1, wherein said polynucleotide further comprises a heterologous promoter.

4. An expression construct comprising one or more of the polynucleotides according to claim 3.

5. A gene silencing molecule, comprising a polynucleotide sequence comprising first and second regions:
   (a) said first region comprising a nucleotide sequence at least 90% identical to a sequence entirely complementary to 60 or more contiguous nucleotides of SEQ ID NO: 1 or 2; and
   (b) said second region comprising a nucleotide sequence entirely complementary to said nucleotide sequence in said first region,
   wherein said gene silencing molecule, when assimilated by a coleopterous pest of plants, inhibits or reduces the proliferation of said pest.

6. The gene silencing molecule according to claim 5, wherein the first and the second region are capable of forming a double-strand region, and wherein said first and second regions are separated in said polynucleotide sequence by a spacer sequence of at least 3 nucleotides.

7. The gene silencing molecule according to claim 6, wherein the spacer sequence is an intron.

8. A vector
   encoding the dsRNA of claim 1,
   wherein said vector further comprises a heterologous sequence.

9. An expression vector that encodes the dsRNA of claim 1.

10. A transformed cell, comprising the polynucleotide according to claim 3.

11. The cell according to claim 10, wherein said cell is a prokaryotic cell.

12. The cell according to claim 10, wherein said cell is a eukaryotic cell.

13. The cell according to claim 10, wherein said cell is a plant or bacterial cell.

14. A transformed plant, comprising the polynucleotide according to claim 3.

15. The plant according to claim 14, wherein said plant, upon ingestion by an insect pest, inhibits or reduces the proliferation of said pest.

16. The plant according to claim 15, wherein the insect pest is selected from the group consisting of *Anthonomus grandis, Diabrotica virgifera, Tenebrio molitor, Tribolium castaneum* and *Hypothenemus hampei, Phoracantha semipunctata, Lixus angustatus, Acanthoscelides obtectus* and other coleoptera that cause damages to woods and agronomically important plants of the families Scolytidae, Cerambycidae, Curculionidae and Bostrichida.

17. A method for producing transgenic eukaryotic organisms, in which the expression of a target gene in the cells of the organism is reduced, wherein said method comprises:
   transforming a cell or cells of the organism with the vector of claim 9, to produce a transgenic cell or cells; and
   growing or regenerating a transgenic eukaryotic organism of the transgenic cell or cells.

18. A method for controlling infestation of coleoptera, wherein said method comprises supplying, in the diet of a coleopterous pest, an agent comprising the polynucleotide of claim 3.

19. The method according to claim 17, wherein the cell or cells further comprise a polynucleotide sequence encoding a pesticidal agent.

20. The method according to claim 19, wherein the pesticidal agent is selected from the group consisting of patatin, an insecticidal protein of *Bacillus thuringiensis*, an insecticidal *Xenorhabdus* protein, an insecticidal *Photorhabdus* protein, an insecticidal *Bacillus laterosporous* protein, an insecticidal *Bacillus sphaericus* protein, and a lignin.

21. The method according to claim 18, wherein the coleopterous pest is selected from the group consisting of *Anthonomus grandis, Diabrotica virgifera, Tenebrio molitor, Tribolium castaneum, Hypothenemus hampei, Phoracantha semipunctata, Lixus angustatus, Acanthoscelides obtectus* and other coleoptera that cause damages to woods and agronomically important plants of the families Scolytidae, Cerambycidae, Curculionidae and Bostrichida.

22. The method according to claim 18,
   wherein said agent, upon being ingested or assimilated by the pest, suppresses or reduces the expression of a gene that performs a function that is essential to the survival of the insect.

23. The method according to claim 22, wherein the function essential to the survival of the insect is selected from the group consisting of differentiation and development of the cuticula, egg formation, larval maturation, transition of larval stage, pupation, digestion and assimilation of nutrients, and protection against pathogens.

24. A method for improving the yield of cultivated plants subject to infestation by insect pests, wherein said method comprises:
   a. introducing the vector of claim 9 into a plant, to produce a transformed plant; and
   b. growing the transformed plant so as to enable expression of the dsRNA molecule encoded by said vector, wherein the expressed dsRNA molecule inhibits or reduces the proliferation of said pest.

25. The method according to claim 24,
   wherein the expressed dsRNA molecule suppresses at least one first target gene in an insect pest that has ingested a portion of said plant, wherein said target gene performs at least one function that is essential to survival of the insect, and wherein said function is selected from the group consisting of differentiation and development of cuticula, eqq formation, larval maturation, larval stage transition, pupation, cell division, energetic metabolism, respiration, and formation and hardening of the cuticula.

26. The method according to claim 25,
   wherein the insect pest is selected from the qroup consistinq of *Anthonomus grandis, Diabrotica virgifera, Tenebrio molitor, Tribolium castaneum, Phoracantha semipunctata, Lixus angustatus, Acanthoscelides obtectus* and other coleoptera that cause damages to woods and agronomically important plants of the families Scolytidae, Cerambycidae, Curculionidae and Bostrichida.

27. A method for producing a commercial product, said method comprising obtaining the plant of claim 14 and preparing a commercial product from the plant.

28. A method of producing a food or animal feed, said method comprising obtaining the plant of claim 14 and preparing a food or animal feed from said plant.

29. A method for controlling infestation of coleoptera, wherein said method comprises supplying, in the diet of a coleopterous pest, an agent comprising the dsRNA of claim 1.

30. An expression vector that encodes the gene silencing molecule of claim 5.

31. A transformed cell, comprising the expression vector of claim 30.

32. The cell according to claim 31, wherein said cell is a prokaryotic cell.

33. The cell according to claim 31, wherein said cell is a eukaryotic cell.

34. The cell according to claim 31, wherein said cell is a plant or bacterial cell.

35. A transformed plant, comprising the expression vector of claim 30.

* * * * *